United States Patent [19]

Regan et al.

[11] Patent Number: 4,996,234
[45] Date of Patent: Feb. 26, 1991

[54] HMG-COA REDUCTASE INHIBITORS

[75] Inventors: John R. Regan, Princeton, N.J.; Kent W. Neuenschwander, Ambler, Pa.

[73] Assignee: Rhone-Poulenc Rorer Pharmaceuticals Inc., Fort Washington, Pa.

[21] Appl. No.: 446,358

[22] Filed: Dec. 5, 1989

Related U.S. Application Data

[60] Division of Ser. No. 328,836, Feb. 13, 1990, Pat. No. 4,900,754, which is a continuation-in-part of Ser. No. 135,805, Dec. 21, 1987, Pat. No. 4,863,957.

[51] Int. Cl.$^5$ ............... A61K 31/19; A61K 31/20; C07C 62/30; C07C 62/04
[52] U.S. Cl. ............... 514/563; 562/469; 562/429; 562/430; 562/431; 562/435; 562/437; 562/438; 562/455; 562/452; 514/559; 514/561; 514/562; 514/563; 514/564; 514/570; 514/824
[58] Field of Search ............... 562/469, 429, 430, 431, 562/435, 434, 437, 438, 455, 452; 514/559, 570, 561, 562, 563, 564, 824

[56] References Cited

U.S. PATENT DOCUMENTS

| | | | |
|---|---|---|---|
| 4,282,155 | 8/1981 | Smith et al. | 549/292 |
| 4,308,378 | 12/1981 | Stokker | 549/292 |
| 4,503,072 | 3/1985 | Hoffman et al. | 514/549 |
| 4,567,289 | 1/1986 | Willard et al. | 560/59 |
| 4,611,067 | 9/1986 | Volank et al. | 556/416 |
| 4,622,338 | 11/1986 | Baran et al. | 549/292 |
| 4,668,699 | 5/1987 | Hoffman et al. | 560/119 |
| 4,681,893 | 7/1987 | Roth | 514/423 |
| 4,772,626 | 9/1981 | Smith et al. | 549/292 |

*Primary Examiner*—Richard L. Raymond
*Assistant Examiner*—Mark W. Russell
*Attorney, Agent, or Firm*—Imre (Jim) Balogh; James A. Nicholson

[57] ABSTRACT

Disclosed are novel 3-hydroxy-3-methylglutaryl-coenzyme A reductase inhibitors useful as antihypercholesterolemic agents represented by the formula

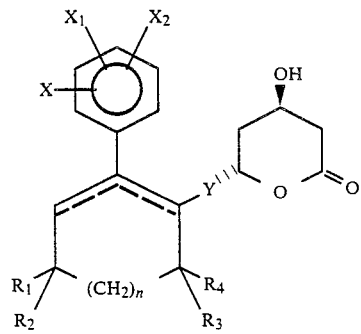

and the corresponding ring-opened hydroxy acids derived therefrom and pharmaceutically acceptable salts thereof.

Pharmaceutical compositions containing said compounds and method of inhibiting the biosynthesis of cholesterol therewith are also disclosed.

8 Claims, No Drawings

HMG-COA REDUCTASE INHIBITORS

This application is a division of co-pending application Ser. No. 328,836, filed on Mar. 27, 1989, now issued as U.S. Pat. No. 4,900,754, which in turn is a continuation-in-part of application Ser. No. 135,805, filed on Dec. 21, 1987, and issued as U.S. Pat. No. 4,863,957.

1. Field of the Invention

The present invention relates to compounds, pharmaceutical compositions and a method useful for reducing serum cholesterol in humans. More particularly, the invention relates to trans-6-[(2-aryl-substituted cycloalkenyl and substituted cycloalkyl)alkenyl and alkyl]-3,4,5,6-tetrahydro-2H-pyran-2-ones, the corresponding ring opened hydroxy acids derived therefrom and pharmaceutically acceptable salts thereof which are potent inhibitors of the enzyme 3-hydroxy-3-methyl-glutaryl-coenzyme A reductase (hereinafter HMG-CoA reductase), pharmaceutical compositions thereof, and a method of inhibiting biosynthesis of cholesterol for the treatment of atherosclerosis, hyperlipidemia and hypercholesterolemia.

2. Related Prior Art

Inhibitors of HMG-CoA are effective in lowering blood plasma cholesterol level as well as inhibiting the biosynthesis of cholesterol in humans. As such, inhibitors of HMG-CoA are useful in the prevention and treatment of coronary heart diseases. The prior art recognizes the importance of such compounds, e.g., Bethridge et al., Brit. Med. J., 4,500 (1975) and Brown et al., Scientific American, 58 Nov. (1984). Illustrative references directed to such compounds follow.

U.S. Pat. No. 4,681,893 to B. D. Roth pertains to trans-6-[2-(3- or 4-carboxamido-substituted pyrrol-1-yl)alkyl]-4-hydroxypyran-2-ones useful as hypochloesterolemic agents.

U.S. Pat. No. 4,668,699 to Hoffman et al. discloses semi-synthetic analogs of compactin and mevinolin and the dihydro and tetrahydro analogs thereof for antihypercholesterolemic application.

U.S. Pat. No. 4,282,155 to Smith et al. is directed to 6(R)-[2-(8'-Etherified-hydroxy-2',6'-dimethylpolyhydronaphthyl-1')ethyl]-4(R)-hydroxy-3,4,5,6-tetrahydro-2H-pyran-2-ones for inhibition of biosynthesis of cholesterol.

U.S. Pat. No. 4,567,289 to Willard et al. relates to methyl, ethyl, n-propyl, 2-(acetylamino)ethyl, or 1-(2,3-dihydroxy)propyl ester of E-(3R,5S)-7-(4'-fluoro-3,3',5-trimethyl[1,1'-biphenyl]-2-yl)-3,5-dihydroxy-6-heptenoic acid that are HMG-CoA reductase inhibitors.

U.S. Pat. No. 4,611,067 to Volante et al. discloses a process for the preparation of HMG-CoA reductase inhibitors which contain a 4-hydroxy-3,4,5,6-tetrahydro-2H-pyran-2-one moiety.

SUMMARY OF THE INVENTION

In accordance with the present invention, certain trans-6-[(2-aryl-substituted cycloalkenyl and substituted cycloalkyl)alkenyl and alkyl]-3,4,5,6-tetrahydro-2H-pyran-2-ones, the corresponding ring-opened hydroxyacids derived therefrom and pharmaceutically acceptable salts thereof are provided which are potent inhibitors of HMG-CoA reductase. Specifically, the invention provides compounds of formula I.

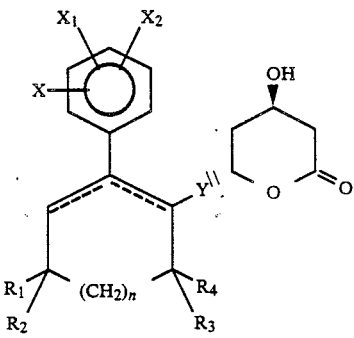

wherein
Y is:
—CHR—,
—CHRCHR—,
—CHRCHRCHR—, or
—RC=CR—;
X, $X_1$ and $X_2$ are independently:
F,
Cl,
Br,
OH,
$CF_3$
R,
alkoxy,
aryl,
$NO_2$,
NH(CO)R,
$N(R)_2$, or
$S(O)_mR$;
$R_1$ and $R_2$ are independently:
H,
alkyl,
aryl,
OR,
F,
Cl, or
Br;
$R_3$ and $R_4$ are independently:
H or lower alkyl;
R is:
H or lower alkyl;
n is:
0–b 2;
m is: 0–2; and
the dotted lines between carbons 1 and 2 or 2 and 3 in the cycloalkyl ring represent an optional double bond.

DETAILED DESCRIPTION OF THE INVENTION

As employed above and throughout the specification, the following terms, unless otherwise indicated, shall be understood to have the following meaning:

"Lower alkyl" means a saturated or unsaturated aliphatic hydrocarbon which may be either straight- or branched-chained containing from 1 to 4 carbon atoms.

"Alkyl" means a saturated or unsaturated aliphatic hydrocarbon which may be either straight-or branched-chained containing from one to ten carbon atoms.

"Alkoxy" means an alkyl oxy group in which "alkyl" is as previously defined. Lower alkoxy groups are preferred which include methoxy, ethoxy, n-propoxy, i-propoxy, sec-propoxy, and n-butoxy.

"Aryl" means an aromatic hydrocarbon radical having 6 to 10 carbon atoms. The preferred aryl groups are phenyl, substituted phenyl and naphthyl. The term "substituted" means "alkyl", "halogen" or "hydroxyalkyl" substitution.

The invention encompasses optical and stereoisomers of the compounds and mixtures thereof defined by the structural formula.

The general procedure for producing the compounds of the present invention is as follows:

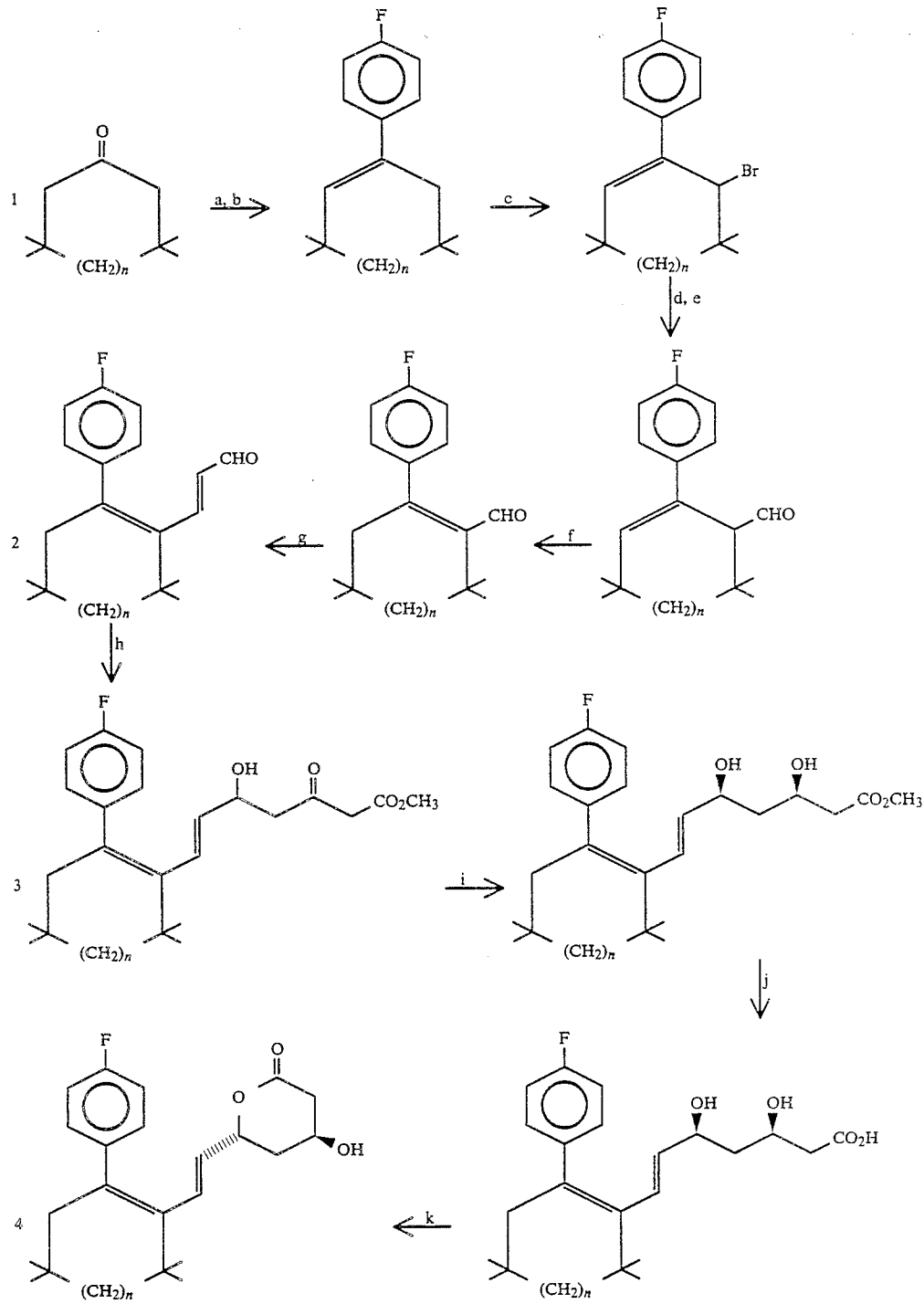

The pharmaceutically acceptable salts of the present invention include those formed from sodium, potassium, calcium, aluminum, lithium, magnesium, zinc, lysine, arginine, procaine, ethylenediamine and piperazine.

Alternatively, steps a through f can be replaced with steps l and m as shown hereunder,

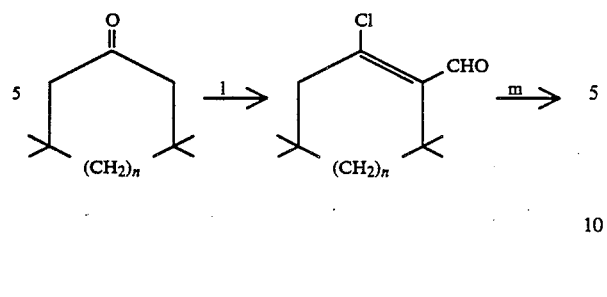
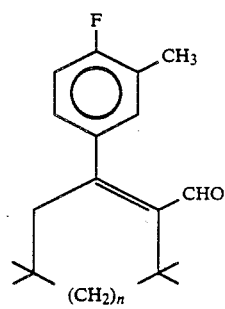
-continued
wherein the symbols used in the reactions denote the following reagents;
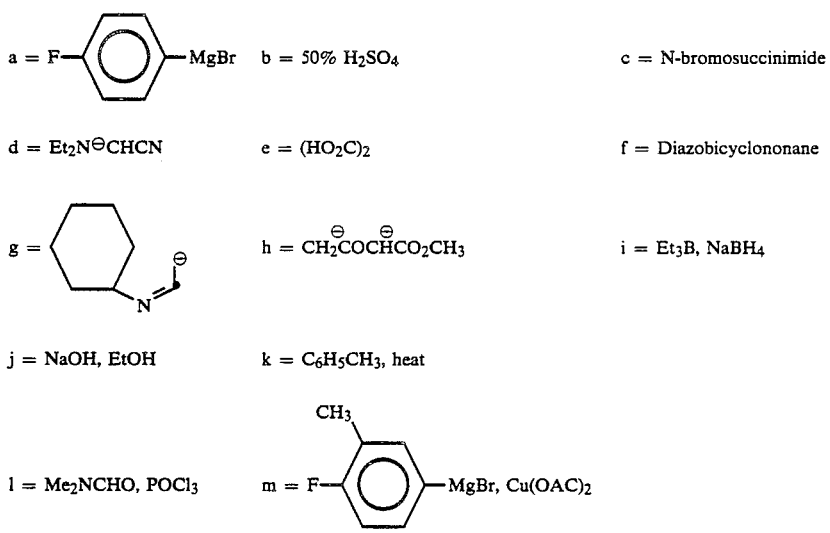
Reaction Sequence II
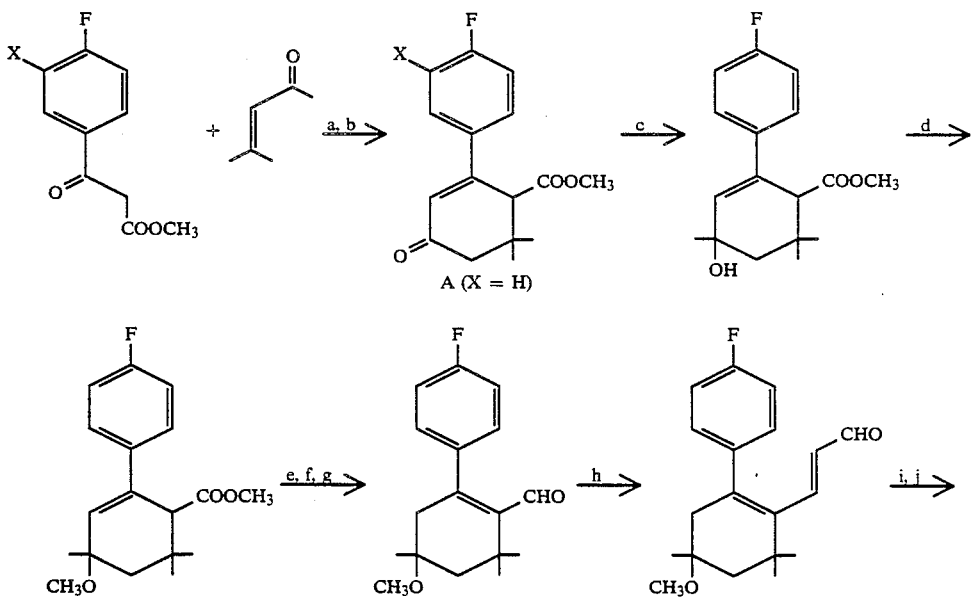

-continued
Reaction Sequence II

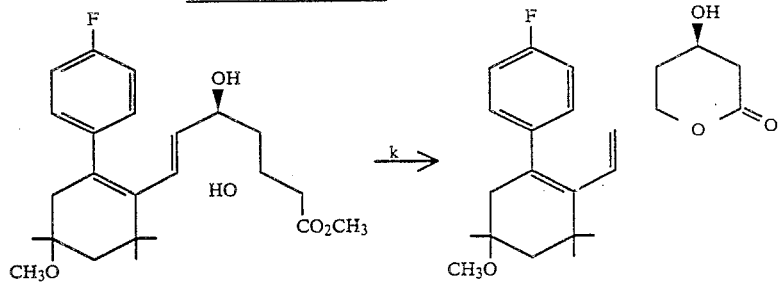

Reaction Sequence III

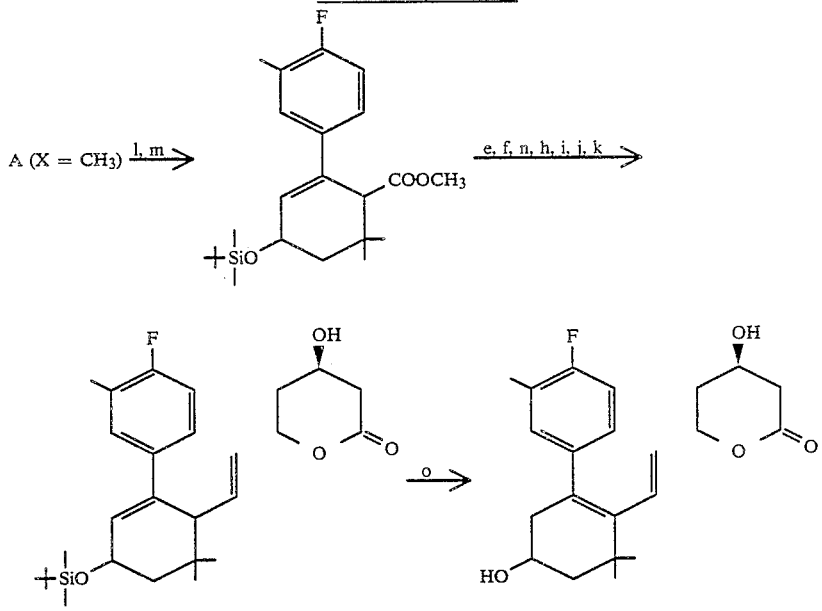

Wherein the symbols used in the reaction denote the following reagents:

| | |
|---|---|
| a. BF$_3$-Etherate | i. CH$_3$COCH$_2$COOCH$_3$/LDA |
| b. Triton B/heat | j. Et$_3$B/NaBH$_4$/Methanol |
| c. Methyl Lithium | k. (1) NaOH (2) DCC/Ether |
| d. Methanol/H$_2$SO$_4$ | l. NaBH$_4$ |
| e. LAH/THF | m. t-Butylchlorodimethylsilane/ imidazole |
| f. SO$_3$-pyridine/DMSO | |
| g. DBN/THF | n. Triton B/cold |
| h. (1) C$_6$H$_{11}$N=CHCH$_3$/LDA (2) SiO$_2$ | O. (n-C$_4$H$_9$)$_4$NF/THF |

The starting materials were obtained from the Aldrich Chemical Co. but they may also be synthesized in accordance with methods known in the art.

The following preparative examples will further illustrate the invention; Examples 1 through 4 being based essentially on Reaction Sequence I; Example 5 on Reaction Sequence II and Example 6 on Reaction Sequence III.

EXAMPLE 1

Step 1:
1-(4-Fluorophenyl)-1-hydroxy-3,3,5,5-tetramethylcyclohexane

A solution of 51.42 g (333.3 mmoles) of 3,3,5,5-tetramethylcyclohexanone in 200 ml of tetrahydrofuran (THF) was added dropwise to an ice cold solution made up of 200 ml of a 2M ether solution of 4-fluorophenyl magnesium bromide (400 mmoles) and 100 ml of THF. The reaction mixture was warmed to room temperature and stirred overnight. The reaction mixture was then poured onto ice and 500 ml of 1N HCl. After stirring for 0.5 hour, the layers were separated. The aqueous layer was extracted once with ether and the combined organic layers were evaporated in vacuo to obtain the title compound in the form of an oil.

Step 2:
1-(4-Fluorophenyl)-3,3,5,5-tetramethylcyclohexene

From Step 1 the resulting oil was treated with 150 ml of ice cold 50% H$_2$SO$_4$. After stirring for 45 min. at room temperature, the reaction mixture was poured onto 900 ml of crushed ice and extracted with ether. The ether layer was extracted with saturated NaHCO$_3$ and brine. The ether was removed in vacuo and the resulting oil was distilled. BP 103°-106° C./1 mm Hg.

Step 3:
1-Bromo-2-(4-fluorophenyl)-4,4,6,6-tetramethylcyclohex-2-ene

N-Bromosuccinimide (19.58 g, 110 mmoles) and benzoylperoxide (2.42 g, 10 mmoles) were added to a 0.5M CCl$_4$ solution of 23.2 g (100 mmoles) of the product from Step 2. The resulting mixture was heated at reflux for 0.5 hour. After cooling, the reaction mixture was filtered and the CCl$_4$ removed in vacuo. The resulting residue was chromatographed on silica gel, using hexane as the eluent. Yield 29.57 g (95.1 mmoles).

Step 4:
2-Diethylamino-2-[2-(4-fluorophenyl)-4,4,6,6-tetramethylcyclohex-2-ene[acetonitrile To a stirred solution of diisopropylamine (18.47 ml, 132 mmoles) in 250 ml of THF at −78° C. under nitrogen was added 48.4 ml (121 mmoles) of a 2.5M hexane solution of n-butyllithium.

After 15 minutes, a 2.0M THF solution of 14.25 ml (110 mmoles) of diethylaminoacetonitrile was added dropwise. After stirring for 15 minutes more, a 2.0M THF solution of the product obtained in Step 3 (100 mmoles) was added and the mixture slowly warmed to room temperature over a 3 hour period. The reaction mixture was poured into H$_2$O and extracted with ether. The organic layer was extracted with brine and the solvent evaporated in vacuo.

Step 5:
2-(4-Fluorophenyl)-4,4,6,6-tetramethylcyclohex-2-ene-1-carboxaldehyde The residue from Step 4 was dissolved in 200 ml of THF and treated with a solution of 60 g of oxalic acid in 200 ml of H$_2$O. The resulting mixture was heated to reflux for 0.5 hour. After cooling, the reaction mixture was poured into H$_2$O and extracted with ether. The ether layer was extracted twice with saturated NaHCO$_3$, evaporated in vacuo and the residue was purified by flash chromatography on silica gel. Overall yield 19.3 g (74.2 mmoles).

Step 6:
2-(4-Fluorophenyl)-4,4,6,6-tetramethylcyclohex-1-ene-1-carboxaldehyde The aldehyde obtained in Step 5 (130 g, 50 mmoles) was dissolved in a solution of 50 ml of THF and 50 ml of ethanol. To this solution was added 0.62 ml (5 mmoles) of 1,5-diazabicyclo-[4,3,0]-non-5-ene and the reaction mixture stirred at room temperature for 50 hours. The reaction mixture then was diluted with ether and extracted with dilute HCl, saturated NaHCO$_3$, and brine. The solvents were evaporated in vacuo and the residue purified by flash chromatography on silica gel.

Step 7:
(E)-3-[2-(4-fluorophenyl)-4,4,6,6-tetramethylcyclohexenyl]-2-propenaldehyde To a stirred solution of diisopropylamine (10.07 ml, 72 mmoles), in 144 ml of THF, at −60° C., under nitrogen, was added 26.4 ml (66 mmoles) of a 2.5M hexane solution of n-butyllithium. After 15 minutes, when the temperature had warmed to −40° C., a 1.0M THF solution of ethylidenecyclohexylamine (7.5 g, 60 mmoles) was added dropwise. The reaction was stirred for 30 minutes, while the temperature rose to −10° C.

After stirring at −10° C. for an additional 10 minutes, the dark orange solution was cooled to −70° C. A 1.0M THF solution of the unsaturated aldehyde prepared in Step 6 (10.4 g, 40 mmoles) was added dropwise, allowed to slowly warm to −10° C. and stirred for an additional hour.

The reaction mixture was poured into H$_2$O and extracted with ether. The organic layer was extracted with brine and the solvents evaporated in vacuo.

The crude intermediate was chromatographed on silica gel with hexane and finally hexane/ethyl acetate (20/1) as eluents. The intermediate 3-hydroxypropylidenecyclohexylamine was hydrolized on the silica gel column to the 2,4-dienal.

Step 8: Methyl (E)-7-[2-(4-fluorophenyl)-4,4,6,6-tetramethylcyclohexenyl]-5-hydroxy-3-oxo-6-heptenoate To a stirred solution of diisopropylamine (12.09 ml, 86.4 mmoles), in 173 ml of THF, at −60° C., under nitrogen was added 31.68 ml (79.2 mmoles) of a 2.5M hexane solution of n-butyl lithium. After 15 minutes, when the temperature had warmed to −40° C., methyl acetoacetate (3.89 ml, 36 mmoles) was added dropwise. The reaction mixture was stirred for 30 minutes while the temperature was allowed to warm to −10° C. to obtain a yellow solution of the dianion.

To the yellow solution of the dianion was added a 0.25M THF solution of 8.58 g (30 mmoles) of the aldehyde prepared in Step 7. The addition took 30 minutes. The reaction mixture was stirred an additional 30 minutes at −10° C., then quenched with 9.47 (165.6 mmoles) of acetic acid in 40 ml of THF. The reaction mixture was poured into ethyl acetate and extracted with H$_2$O, saturated NaHCO$_3$ and brine.

The residue was purified by flash chromatography on silica gel with hexane/ethyl acetate (5/1) as the eluent.

Step 9: Methyl (E)-7-[2-(4-fluorophenyl)-4,4,6,6-tetramethylcyclohexenyl]-3,5-dihydroxy-6-heptenoate The 5-hydroxy-3-keto ester (10.02 g, 24 mmoles) prepared in Step 8 was dissolved in 60 ml of dry THF and treated with triethylborane (1M in THF, 36 ml, 36 mmoles). After aging for 5 minutes at room temperature, the reaction mixture was cooled to −98° C. (MeOH-liquid N$_2$ bath). Sodium borohydride (1.04 g, 27.6 mmoles) was added, followed by dropwise addition of methanol (24 ml) over a 30 minute period. The reaction mixture was stirred for 30 minutes at −98° C. and over the next 30 minutes was allowed to warm to −60° C. At −60° C. the reaction mixture was quenched by the dropwise addition of 30% H$_2$O$_2$ (50 ml) in H$_2$O (125 ml).

The reaction mixture then was warmed to room temperature and stirred for 30 minutes. It was poured into 1 liter ethyl acetate and extracted with 620 ml of 1N HCl. The organic layer was washed with saturated NaHCO$_3$ and brine.

Step 10:
(E)-7-[2-(4-fluorophenyl)-4,4,6,6-tetramethylcyclohexenyl]-3,5-dihydroxy-6-heptenoic acid A 1N NaOH solution (30 ml, 30 mmoles) was added to a solution of the 3,5-dihydroxyester prepared in Step 9 (9.70 g, 24 mmoles) and 60 ml of ethanol. After stirring for 10 minutes, the ethanol was evaporated in vacuo. The residue was redissolved in H$_2$O and extracted twice with ether. The aqueous layer was acidified with 33 ml of 1N HCl and extracted twice with H$_2$CCl$_2$. The H$_2$CCl$_2$ was removed in vacuo.

Step 11:
Trans-(E)-6-[2-[2-(4-fluorophenyl)-4,4,6,6-tetramethylcyclohexenyl]ethenyl]-3,4,5,6-tetrahydro-4-hydroxy-2H-pyran-2-one The 3,5-dihydroxycarboxylic acid from Step 10 (9.0 g, 23 mmoles) and 250 ml of toluene were refluxed in a Dean-Stark apparatus for 1.5 hours. The toluene was removed in vacuo and the residue chromatographed on silica gel using hexane/ethyl acetate (3/1) as the eluent. The product was recrystallized from ether/hexane. M.P. 121°–122° C.

Step 12:
(E)-7-[2-(4-fluorophenyl)-4,4,6,6-tetramethylcyclohexenyl]-3,5-dihydroxy-6-heptenoic acid sodium salt To a solution of 1.17 g (3.14 mmoles) of the lactone prepared in Step 11, and 21 ml of ethanol was added 3.14 ml of 1N NaOH (3.14 mmoles). After stirring for 30 minutes, the ethanol was removed in vacuo. The residue was redissolved in 50 ml of HPLC grade H$_2$O and extracted twice with hexane. The water layer was freeze-dried to yield a white powder. M.P. 160°–190° C. (dec).

EXAMPLE 2

Referring to steps l and m of Reaction Sequence I, the following process can also be used to advantage subsequent to which the process described in steps 7 through 11 in Example 1 are to be followed.

Step 1:
2-Chloro-4,4,6,6-tetramethylcyclohex-1-ene-1-carboxaldehyde

Phosphorus oxychloride (46.6 ml, 500 mmoles) was added dropwise over a 45 minute period, to an ice cold solution of 47.69 g (652 mmoles) of dimethylformamide and 145 ml of trichloroethylene. The reaction mixture was warmed to room temperature and stirred an additional 1.5 hours. To the resulting reaction mixture was added dropwise a solution of 77.13 g (500 mmoles) of 3,3,5,5-tetramethylcyclohexanone in 145 ml of trichloroethylene.

The reaction mixture was heated to 70° C. for 5 hours, then cooled and stirred overnight at room temperature.

The reaction mixture was cooled in an ice bath and treated dropwise with a solution of 185 g (2.25 moles) of sodium acetate in 400 ml of H$_2$O. The resulting layers were separated and the organic layer was washed once with 500 ml of H$_2$O and twice with 250 ml of brine. After drying over anhydrous sodium sulfate the mixture was filtered and the trichloroethylene removed in vacuo. The concentrate was distilled through a vacuum-jacketed Vigreux column. BP 66°–70° C./1 mm Hg; Yield 26.4 (132 mmoles) of a light yellow oil.

Step 2:
2-(4-Fluoro-3-methylphenyl)-4,4,6,6-tetramethylcyclohex-1-ene-1-carboxaldehyde A Grignard reagent, freshly prepared from 55.96 g (296 mmoles) of 3-bromo-6-fluorotoluene, 11.39 ml (131.6 mmoles) of dibromoethane, and 13.0 g (534.5 mmoles) of magnesium powder in 400 ml of dry THF was added slowly in an ice cold solution, under nitrogen, of 6.57 g (32.9 mmoles) of copper (II) acetate monohydrate, 26.4 g (131.6 mmoles) of 2-chloro-4,4,6,6-tetramethylcyclohex-1-ene-1-carboxaldehyde and 395 ml of dry THF.

During the addition of the Grignard reagent, the reaction mixture changed in color, from blue to a light yellow and finally a dark purple.

The addition took 2 hours and after stirring an additional 0.5 hour, at 0° C., the reaction was poured into 1 liter of saturated ammonium chloride. The organic layer was extracted with H$_2$O, brine, and dried over anhydrous magnesium sulfate. After filtering, the solution was concentrated in vacuo and the residue chromatographed on silica gel with hexane/ethyl acetate (40/1) as the eluent. Yield 17.85 g (65 mmoles).

Employing the general methods detailed in Examples 1 and 2 the following compounds were prepared:

trans-6-[2-[2-(4-chlorophenyl)-4,4-dimethyl-6,6-diethylcyclohex-1-ene]ethyl]-3,4,5,6-tetrahydro-4-hydroxy-2H-pyran-2-one;

trans-6-[2-[trans-2-(4-methylphenyl)-4,4,6,6-tetraethylcyclohexane]ethyl]-3,4,5,6-tetrahydro-4-hydroxy-2H-pyran-2-one;

(E)-7-[2-(4-fluoro-3-methylphenyl)-4,4-diethyl-6,6-dimethylcyclohex-2-ene]-3,5-dihydroxy-6-heptenoic acid;

7-[2-(3,4-dichlorophenyl)-4,4-dibutyl-6,6-dimethylcyclo-hex-1-ene]-3,5-dihydroxyheptanoic acid sodium salt;

ethyl-(E)-7-[cis-2-(3,5-dimethylphenyl)4,4-diphenyl-6,6-dimethylcyclohexane]-3,5-dihydroxy-6-heptenoate;

trans-(E)-6-[2-[2-(4-fluorophenyl)-4,4-dipropyl-6,6-dimethylcyclohex-1-ene]-ethenyl]-3,4,5,6-tetrahydro-4-hydroxy-2H-pyran-2-one;

trans-6-[2-[2-(4-chlorophenyl)-4,4-dimethyl-6,6-diethylcyclohex-1-ene]ethyl]-3,4,5,6-tetrahydro-4-hydroxy-2H-pyran-2-one;

trans-6-[2-[trans-2-(4-methylphenyl)-4,4,6,6-tetraethylcyclohexane]ethyl]-3,4,5,6-tetrahydro-4-hydroxy-2H-pyran-2-one; and trans-(E)-6-[2-{2-(4-fluoro-3-methylphenyl)-4,4,6,6-tetramethylcyclohex-1-ene}ethenyl]-3,4,5,6-tetrahydro-4-hydroxy-2H-pyran-2-one.

EXAMPLE 3

Using the starting materials 3,3,4,4-tetramethylcyclopentanone, 3-ethyl-4,4-dimethylcyclopentanone, 3-phenyl-4,4-diethylcyclopentanone, 3,4-diethylcyclopentanone and essentially following the process of either Example 1 or Example 2 the following five membered ring compounds can be made, respectively:

trans-(E)-6-[2-{2-(4-fluorophenyl)-4,4,5,5-tetramethylcyclopent-1-ene}ethenyl]-3,4,5,6-tetrahydro-4-hydroxy-2H-pyran-2-one;

trans-(E)-6-[2-{2-(4-fluorophenyl)-4-ethyl-5,5-dimethylcyclopent-1-ene}ethenyl]-3,4,5,6-tetrahydro-4-hydroxy-2H-pyran-2-one;

(E)-7-[2-(4-fluorophenyl)-4-phenyl-5,5-dimethylcyclopent-1-ene]-3,5-dihydroxy-6-heptenoic acid sodium salt; and (E)-7-[2-(4-fluorophenyl)-4,5-diethylcyclopent-1-ene]-3,5-dihydroxy-6-heptenoic acid sodium salt.

EXAMPLE 4

Using the starting materials 3,3,6,6-tetramethylcycloheptanone, 3-phenyl-6,6-dimethylcycloheptanone, 3,6-dimethylcycloheptanone, 3,3-diethyl-6,6-dimethylcycloheptanone, and essentially following the process of either Example 1 or Example 2 the following seven membered ring compounds can be made, respectively:

trans-(E)-6-[2-{2-(4-fluorophenyl)-4,4,7,7-tetramethylcyclohept-1-ene}ethenyl]-3,4,5,6-tetrahydro-4-hydroxy-2H-pyran-2-one;

trans-(E)-6-[2-{2-(4-fluorophenyl)-4-phenyl-7,7-dimethylcyclohept-1-ene}ethenyl]-3,4,5,6-tetrahydro-4-hydroxy-2H-pyran-2-one;

(E)-7-[2-(4-fluorophenyl)-4,7-dimethylcyclohept-1-ene]-3,5-dihydroxy-6-heptenoic acid sodium salt; and (E)-7-[2-(4-fluorophenyl)-4,4-diethyl-7,7-dimethylcyclohept-1ene]-3,5-dihydroxy-6-heptenoic acid sodium salt.

EXAMPLE 5

Step 1: Methyl 2-(4-fluorophenyl)-4-oxo-6,6-dimethylcyclohex-2-en-1-carboxylate A solution of methyl 4-fluorobenzoylacetate (20.03 g, 97 mmoles), mesityl oxide (14.58 g, 0.145 moles) and borontrifluoride etherate (13.77 g, 97 mmoles) was kept at 0° C. for 3 days and diluted with ether and saturated NaHCO$_3$. The organic layer was washed with brine and dried (MgSO$_4$). Removal of the volatiles in vacuo provided a residue which was diluted with 200 ml anhydrous methanol and 20 ml of Triton-B. The mixture was heated at reflux 2 hours, cooled, acidified with aqueous HCl and extracted with ether. The organic layers were washed with aqueous HCl, water and brine and dried (MgSO$_4$). Removal of the volatiles in vacuo provided a residue which was purified by HPLC using 8% ethyl acetate in hexanes as the eluent. Concentration in vacuo of the product-rich fractions provided 14.9 g of the oily product.

Step 2: Methyl 2-(4-fluorophenyl)-4-hydroxy-4,6,6-trimethylcyclohex-2-en-1-carboxylate To a −78° C. solution of the above prepared methyl 4-oxocyclohex-2-en-1-carboxylate (11.65 g, 42.2 mmoles) in 100 ml anhydrous THF was added methyl lithium (36.2 ml of a 1.4M solution in ether) dropwise. The solution was stirred 30 minutes and diluted with ether and H$_2$O. The organic layer was washed with brine and dried (MgSO$_4$). Removal of the volatiles in vacuo provided a residue which was purified by HPLC using 11% ethyl acetate in hexanes as the eluent. Concentration in vacuo of the product-rich fractions provided 7.92 g of the oily product.

Step 3: Methyl 2-(4-fluorophenyl)-4-methoxy-4,6,6-trimethylcyclohex-2-en-1-carboxylate To a 0° C. solution of the above prepared alcohol (5.2 g) in 50 ml anhydrous methanol was added H$_2$SO$_4$ (2 ml of a 2% methanol solution). The mixture was stirred 5 hours, diluted with ether, washed with H$_2$O and brine and dried (MgSO$_4$). Removal of the volatiles in vacuo provided a residue which was purified by HPLC using 6% ethyl acetate in hexanes. Concentration in vacuo of the product-rich fractions furnished 4.1 g of the oily product.

Step 4: 2-(4-Fluorophenyl)-4-methoxy-4,6,6-trimethylcyclohex-2-en-1-carboxaldehyde To a solution of the above prepared methyl cyclohex-2-en-1-carboxylate (4.10 g, 13.4 mmoles) in 40 ml anhydrous THF at 0° C. was added portionwise lithium aluminum hydride (LAH) (1.02 g, 26.8 mmoles). The mixture was stirred 2 hours, quenched sequentially with H$_2$O (1 ml), 15% NaOH (1 ml) and H$_2$O (3 ml) and filtered. The filtrate was washed with H$_2$O and brine and dried (MgSO$_4$). Removal of the volatiles in vacuo provided the oily alcohol. To the alcohol and triethylamine (8.82 g, 87.1 mmoles) in 40 ml anhydrous DMSO was added sulfur trioxide pyridine (6.40 g, 40.2 mmoles) in 40 ml DMSO. The mixture was stirred 45 minutes at room temperature, diluted with ether and washed with H$_2$O and brine and dried (MgSO$_4$). Removal of the volatiles in vacuo provided a residue which was purified by HPLC using 5% ethyl acetate in hexanes as the eluent. Concentration in vacuo of the product-rich fractions provided the oily product.

Step 5: 2-(4-Fluorophenyl)-4-methoxy-4,6,6-trimethylcyclohex-1-en-1-carboxaldehyde A solution of the above prepared cyclohex-2-en-1-carboxaldehyde (1.44 g) and 1,5-diazobicyclo[4.3.0]-non-5-ene (150 μl) in 15 ml anhydrous THF was stirred at room temperature for 1 hour and the volatiles were removed in vacuo. Purification of the residue on SiO$_2$ with 5% ethyl acetate in hexanes as the eluent provided 1.20 g of the oily product.

Step 6: (E)-3-[2-(4-fluorophenyl)-4-methoxy-4,6,6-trimethylcyclohex-1-en-1-yl]propenal To a 0° C. solution of LDA (8.84 mmoles) in 10 ml THF was added dropwise a solution of ethylidenecyclohexylamine (Org. Syn. 50 66) (1.11 g, 8.84 mmoles) in 10 ml THF. The mixture was stirred 30 minutes, cooled to −78° C. and a solution of the above prepared cyclohex-1-en-1-carboxaldehyde (1.28 g, 4.65 mmoles) in 20 ml THF was added. The solution was stirred at −30° C. for 3 hours and diluted with ether and H$_2$O. The organic layer was washed with brine and dried (MgSO$_4$). Removal of the volatiles in vacuo provided a residue which was hydrolyzed and purified by HPLC using 15% ethyl acetate in hexanes as the eluent. Concentration in vacuo of the product-rich fractions provided 1.31 g of the oily product.

Step 7: Methyl (E)-7-[2-(4-fluorophenyl)-4-methoxy-4,6,6-trimethylcyclohex-1-en-1-yl]-5-hydroxy-3-oxohept-6-enoate To a −60° C. solution of LDA (11.6 mmoles) in 30 ml anhydrous THF was added dropwise methyl acetoacetate (0.601 g, 5.18 mmoles) in 5 ml THF. The solution was stirred for 60 minutes at −10° C. and the above prepared propenal (1.3 g, 4.31 mmoles) in 15 ml THF was added. The mixture was stirred 60 minutes at 0° C. and diluted with ether and aqueous HCl. The organic layer was washed with aqueous NaHCO$_3$ and brine and dried (MgSO$_4$). Removal of the volatiles in vacuo provided a residue which was purified by HPLC using 25% ethyl acetate in hexanes as the eluent. Concentration in vacuo of the product-rich fractions furnished 1.08 g of the oily product.

Step 8: Methyl (E)-7-[2-(4-fluorophenyl)-4-methoxy-4,6,6-trimethylcyclohex-1-en-1-yl]-3,5-dihydroxyhept-6-enoate To a solution of the above prepared 5-hydroxy-3-oxohept-6-enoate ester (1.08 g, 2.6 mmoles) in THF was added triethylborane (3.9 ml of a 1M solution in THF).

The mixture was stirred for 5 minutes, cooled to −78° C. and sodium borohydride (0.113 g, 29.9 mmoles) was added. Anhydrous methanol (2 ml) was added dropwise over 15 minutes and the mixture stirred for 60 minutes and quenched with aqueous $H_2O_2$. The solution was warmed to room temperature, stirred 1 hour and diluted with ether and $H_2O$. The organic layer was washed with brine and dried ($MgSO_4$). Removal of the volatiles in vacuo provided the oily product (1.08 g).

Step 9:
Trans-(E)-6-[2-[2-(4-fluorophenyl)-4-methoxy-4,6,6-trimethylcyclohex-1-en-1-yl]ethenyl]-4-hydroxy-3,4,5,6-tetrahydro-2H-pyran-2-one To a solution of the above prepared ester (1.08 g) in 10 ml methanol at 0° C. was added aqueous NaOH (2.6 ml of a 1N solution). The mixture was stirred for 3 hours, acidified to pH 3 with aqueous HCl and extracted with ether. The combined organic extracts were washed with $H_2O$ and brine and dried ($MgSO_4$). Removal of the volatiles in vacuo provided the carboxylic acid (0.77 g). To a solution of the acid in anhydrous ether at 0° C. was added dicyclohexylcarbodiimide (0.395 g). The mixture was stirred 4 hours, filtered and the volatiles removed in vacuo. Purification of the residue with $SiO_2$ using 40% ethyl acetate in hexanes as the eluent provided the product having an m.p. of 100°–4° C.

EXAMPLE 6

Step 1:
1-Hydroxymethyl-2-(4-fluoro-3-methylphenyl)-4-t-butyldimethylsiloxy-6,6-dimethylcyclohex-2-ene To a 0° C. solution of methyl 2-(4-fluoro-3-methylphenyl)-4-oxo-6,6-dimethylcyclohex-2-en-1-carboxylate (13.7 g, 47.2 mmoles) in 100 ml methanol was added portionwise sodium borohydride (1.5 molar equivalents). The mixture was stirred 1 hour, diluted with ether and $H_2O$. The organic layer was washed with water and brine and dried ($MgSO_4$). Removal of the volatiles in vacuo provided the alcohol. To a solution of imidazole (9.75 g, 142 mmoles) in 125 ml $CH_2Cl_2$ was added t-butylchlorodimethylsilane (11.0 g, 70.8 mmoles) in 125 ml $CH_2Cl_2$. The mixture was stirred 15 minutes and the above alcohol in $CH_2Cl_2$ was added. The mixture was stirred overnight, diluted with ether, washed with $H_2O$ and brine and dried ($MgSO_4$). Removal of the volatiles in vacuo provided the oily product. To a solution of the above prepared ester in 250 ml anhydrous THF at 0° C. was added portionwise LAH (3.60 g, 94.4 mmoles). The reaction was stirred overnight while slowly warming to room temperature, quenched with $H_2O$ (3.6 ml), 15% NaOH (3.6 ml) and $H_2O$ (10.8 ml) and filtered. The filtrate was washed with brine and dried ($MgSO_4$). Removal of the volatiles in vacuo provided a residue which was purified by HPLC using 11% ethyl acetate in hexanes as the eluent. Concentration in vacuo of the product-rich fractions furnished 6.55 g of the oily product.

Step 2:
(E)-3-[2-(4-fluoro-3-methylphenyl)-4-t-butyldimethylsiloxy-6,6-dimethylcyclohex-1-en-1-yl]propenal To a solution of the above prepared alcohol (43.5 g, 0.115 moles) and triethylamine (75.7 g, 0.748 moles) in 300 ml anhydrous DMSO was added sulfur trioxide pyridine complex (56.0 g, 0.345 moles) in 400 ml DMSO. The solution was stirred 2 hours, diluted with ether, washed with $H_2O$ and brine and dried ($MgSO_4$). Removal of the volatiles in vacuo provided 21.6 g of the oily aldehyde. The aldehyde was dissolved in 250 ml anhydrous THF and potassium t-butoxide (320 mg) was added. The solution was stirred 30 minutes and diluted with ether and water. The organic layer was washed with dilute aqueous acetic acid and brine and dried ($MgSO_4$). Removal of the volatiles in vacuo provided 20.2 g of the oily aldehyde. To a −78° C. solution of LDA (0.102 moles) in anhydrous THF was added ethylidenedicyclohexylamine (12.8 g, 0.102 moles). The mixture was stirred at 0° C. 60 minutes, cooled to −78° C. and treated with the above aldehyde (53.6 mmoles) in THF. The solution was stirred 90 minutes and quenched with $H_2O$ and ether. The organic layer was washed with $H_2O$ and brine and dried ($MgSO_4$). Removal of the volatiles in vacuo provided a residue which was hydrolyzed and purified by HPLC using 3% ethyl acetate in hexanes as the eluent. Concentration in vacuo of the product-rich fractions provided 13.5 g of the oily product.

Step 3: Methyl (E)-7-[2-(4-fluoro-3-methylphenyl)-4-t-butyldimethylsiloxy-6,6-dimethylcyclohex-1-en-1-yl]-5-hydroxy-3-oxohept-6-enoate The above prepared propenal (13.45 g, 33.4 mmoles) was treated With the LDA-derived dianion of methyl acetoacetate (4.66 g, 40.1 mmoles) at 0° C. for 60 minutes and worked up in the usual way. Purification of the residue by HPLC using 20% ethyl acetate in hexanes as the eluent provided 7.8 g of the oily product.

Step 4: Methyl (E)-7-[2-(4-fluoro-3-methylphenyl)-4-t-butyldimethylsiloxy-6,6-dimethylcyclohex-1-en-1-yl]-3,5-dihydroxyhept-6-enoate The above prepared methyl 5-hydroxy-3-oxohept-6-enoate (7.8 g, 15.1 mmoles) was treated with triethylborane (22.6 mmoles), sodium borohydride (0.654 g, 17.3 mmoles) and methanol (10 ml) in anhydrous THF at −78° C. Following the usual work up and purification of the residue on HPLC, using ethyl acetate and hexanes as the eluent, provided the oily product.

Step 5:
Trans-(E)-6-[2-[2-(4-fluoro-3-methylphenyl)-4-t-butyldimethylsiloxy-6,6-dimethylcyclohex-1-en-1-yl]ethenyl]-4-hydroxy-3,4,5,6-tetrahydro-2H-pyran-2-one The above prepared 3,5-dihydroxyhept-6-enoate ester was treated with 1.5 molar equivalents of sodium hydroxide (1N aqueous solution) in methanol at room temperature for 30 minutes, cooled to 0° C., acidified with aqueous HCl to pH 2-3 and diluted with ether. The organic layer was washed with $H_2O$ and brine and dried ($MgSO_4$). Removal of the volatiles in vacuo provided a residue which was diluted with ether and cooled to 0° C. To this solution was added 1 molar equivalent of dicyclohexylcarbodiimide and 0.05 molar equivalent of 4-dimethylaminopyridine. The mixture was stirred 3 hours, diluted with ether and filtered. The filtrate was concentrated in vacuo and the residue was purified by $SiO_2$ chromatography using 33% ethyl acetate in hexanes as the eluent. Concentration in vacuo of the product-rich fractions provided the product.

Step 6:
Trans-(E)-6-[2-[2-(4-fluoro-3-methylphenyl)-4-hydroxy-6,6-dimethylcyclohex-1-en-1-yl]ethenyl]-4-hydroxy-3,4,5,6-tetrahydro-2H-pyran-2-one A solution of the above prepared silyl ether and 2 molar equivalents of tetrabutylamonium fluoride (1M solution in THF) in 5% acetic acid in THF was stirred overnight at room temperature and diluted with ether and H$_2$O. The organic layer was washed with H$_2$O, saturated NaHCO$_3$ and brine and dried (MgSO$_4$). Removal of the volatiles in vacuo provided a residue which was purified by HPLC using 20% ethyl acetate in hexanes as the eluent. Concentration in vacuo of the product-rich fractions provided the solid product. m.p. 77°–9° C.

Employing the methods of Examples 5 and 6 the following compounds can be prepared:

trans-(E)-6-[2-[2-(4-fluoro-3,5-dimethylphenyl)-4-hydroxy-6,6-dimethylcyclohex-1-en-1-yl]ethenyl]-4-hydroxy-3,4,5,6-tetrahydro-2H-pyran-2-one;

trans-(E)-6-[2-[2-(4-fluorophenyl)-4-hydroxy-4,6,6-trimethylcyclohex-1-en-1-yl]ethenyl]-4-hydroxy-3,4,5,6-tetrahydro-2H-pyran-2-one;

trans-(E)-6-[2-[2-(4-fluoro-3-methylphenyl)-4-methoxy-6,6-dimethylcyclohex-1-en-1-yl]ethenyl]-4-hydroxy-3,4,5,6-tetrahydro-2H-pyran-2-one;

trans-(E)-6-[2-[2-(4-fluoro-3-methylphenyl)]-4-methoxy-4,6,6-trimethylcyclohex-1-en-1-yl]ethenyl]-4-hydroxy-3,4,5,6-tetrahydro-2H-pyran-2-one;

trans-(E)-6-[2-[2-(4-fluoro-3-methylphenyl)-4-butoxy-4,6,6-trimethylcyclohex-1-en-1-yl]ethenyl]-4-hydroxy-3,4,5,6-tetrahydro-2H-pyran-2-one;

trans-(E)-6-[2-[2-(4-nitrophenyl)-4-hydroxy-5,5-dimethylcyclopent-1-en-1-yl]ethenyl]-4-hydroxy-3,4,5,6-tetrahydro-2H-pyran-2one;

trans-(E)-6-[2-[2-(4-nitro-3-methylphenyl)-4-methoxy-5,5-dimethylcyclopent-1-en-1-yl]ethenyl]-4-hydroxy-3,4,5,6-tetrahydro-2H-pyran-2-one;

trans-(E)-6-[2-[2-(4-dimethylaminophenyl)-4-hydroxy-4,6,6-trimethylcyclohex-1-en-1-yl]ethenyl]-4-hydroxy-3,4,5,6-tetrahydro-2H-pyran-2-one;

trans-(E)-6-[2-[2-(4-ethylthio-3-fluorophenyl)-4-propoxy-6,6-dimethylcyclohex-2-en-1-yl]ethenyl]-4-hydroxy-3,4,5,6-tetrahydro-2H-pyran-2-one;

trans-(E)-6-[2-[2-(4-butylsulfonyl-3-methylphenyl)-4-hydroxy-7,7-dimethylcyclohept-1-en-1-yl]ethenyl]-4-hydroxy-3,4,5,6-tetrahydro-2H-pyran-2-one;

trans-(E)-6-[2-[2-(3-acetamidophenyl)-4-methoxy-4,7,7-triethylcyclohept-1-en-1-yl]ethenyl]-4-hydroxy-3,4,5,6-tetrahydro-2H-pyran-2-one;

trans-(E)-6-[2-[2-(4-fluoro-3-propionamidophenyl)-4-hydroxy-6,6-dimethylcyclohex-1-en-1-yl]ethenyl]-4-hydroxy-3,4,5,6-tetrahydro-2H-pyran-2-one;

trans-(E)-6-[2-[2-(4-chloro-3-ethylphenyl)-4-(1,1-dimethylethoxy)-6,6-dimethylcyclohex-1-en-1-yl]ethenyl]-4-hydroxy-3,4,5,6-tetrahydro-2H-pyran-2-one;

trans-6-[2-[2-(4-fluorophenyl)-4-hydroxy-6,6-dimethylcyclohex-1-en-1-yl]ethyl]-4-hydroxy-3,4,5,6-tetrahydro-2H-pyran-2-one;

trans-6-[2-[2-(5-dimethylamino-4-fluoro-3-methylphenyl)-4-ethoxy-4,6,6-trimethylcyclohex-1-en-1-yl]ethyl]-4-hydroxy-3,4,5,6-tetrahydro-2H-pyran-2-one;

(E)-7-[2-(4-fluoro-3,5-dimethylphenyl)-4-methoxy-4-methyl-6,6-diethylcyclohex-1-en-1-yl]-3,5-dihydroxyhept-6-enoic acid sodium salt;

trans-6-[2-[2-(4-fluoro-3-methylphenyl)-4-hexyloxy-6-ethyl-6-methylcyclohex-1-en-1-yl]ethyl]-4-hydroxy-3,4,5,6-tetrahydro-2H-pyran-2-one;

trans-(E)-6-[2-[2-(5-chloro-4-acetamido-3-methylphenyl)-4-hydroxy-6,6-dimethylcyclohex-1-en-1-yl]ethenyl]-4-hydroxy-3,4,5,6-tetrahydro-2H-pyran-2-one;

(E)-7-[2-(4-methylthio-3-methylphenyl)-4-methoxy-6,6-dimethylcyclohex-1-en-1-yl]-3,5-dihydroxyhept-6-enoic acid sodium salt;

(E)-7-[2-(4-acetamido-3-ethylsulfonylphenyl)-4-hydroxy-6,6-diethylcyclohex-1-en-1-yl]-3,5-dihydroxyhept-6-enoic acid; and trans-6-[2-[2-(4-dipropylamino-3-propylphenyl)-4-propoxy-4,6,6-trimethylcyclohex-1-en-1-yl]ethyl]-4-propoxy-3,4,5,6-tetrahydro-2H-pyran-2-one.

The compounds of the present invention are useful as hypocholesterolemic or hypolipidemic agents by virtue of their ability to inhibit the biosynthesis of cholesterol through inhibition of the enzyme HMG-CoA reductase. Having such ability, the compounds are incorporated into pharmaceutically acceptable carriers and administered to a patient in need of such cholesterol biosynthesis inhibition orally or parenterally. Such pharmaceutical formulations to contain at least one compound according to the invention.

Suitable carriers include diluents or fillers, sterile aqueous media and various non-toxic organic solvents. The compositions may be formulated in the form of tablets, capsules, lozenges, trochees, hard candies, powders, aqueous suspensions, or solutions, injectable solutions, elixirs, syrups and the like and may contain one or more agents selected from the group including sweetening agents, flavoring agents, coloring agents and preserving agents, in order to provide a pharmaceutically acceptable preparation.

The particular carrier and the ratio of active compound to carrier are determined by the solubility and chemical properties of the compounds, the particular mode of administration and standard pharmaceutical practice. For example, excipients such as lactose, sodium citrate, calcium carbonate and dicalcium phosphate and various disintegrants such as starch, alginic acid and certain complex silicates, together with lubricating agents such as magnesium stearate, sodium lauryl sulphate and talc, can be used in producing tablets. For a capsule form, lactose and high molecular weight polyethylene glycols are among the preferred pharmaceutically acceptable carriers.

Where aqueous suspensions for oral use are formulated, the carrier can be emulsifying or suspending agents. Diluents such as ethanol, propylene glycol, and glycerin and their combinations can be employed as well as other materials.

For parenteral administration, solutions or suspensions of these compounds in aqueous alcoholic media or in sesame or peanut oil or aqueous solutions of the soluble pharmaceutically acceptable salves can be employed.

The dosage regimen in carrying out the methods of this invention is that which insures maximum therapeutic response until improvement is obtained and thereafter the minimum effective level which gives relief. Doses may vary, depending on the age, severity, body weight and other conditions of the patients but are ordinarily in the area of 5 mg/kg to 500 mg/kg of body weight in oral administration; such may, of course be given in two to four divided doses. With other forms of administration equivalent or adjusted doses will be administered depending on the route of administration.

The utility of the claimed compounds is measured by the test methods described hereunder. The methods are based on the articles: "Purification of 3-hydroxy-3-methylgutaryl coenzyme A reductase from rat liver" by Kleinsek et al., Proc. Natl. Acad. Sci. U.S.A., Vol. No. 4, pp. 1431–1435, April 1977 Biochemistry; "Mevinolin: A highly potent competitive inhibitor of hydroxy methyl glutaryl-coenzyme A reductase and a cholesterol-lowering agent" by Alberts et al., Proc. Natl. Acad. Sci. U.S.A., Vol 77, pp. 3951–3961, July 1980, Biochemistry; "Effects of ML-236B on cholesterol metabolism in mice rats: Lack of hypocholesterolemic activity in normal animals" by Ends et al., Biochimica et Biophysica Acta, 575 (1979) 266–276; and "Evidence of regulation of 3-hydroxy-3-methylglutaryl-coenzyme A reductase activity and cholesterol synthesis in monhepatic tissues of rat") by Balasubramaniam et al., Proc. Natl. Acad. Sci. U.S.A., Vol. 73, No. 8, pp. 2564–2568, August 1976, Biochemistry.

The first method used (designated HMGR Screen) was as follows. Male rats were acclimated to an alternate 12 hour light-dark cycle for a period of 2–3 weeks. The animals, weighing 180–230 g, were fed ad libitum a rat chow containing 2% cholestyramine for 5 days prior to sacrifice at the mid-dark period. Liver microsomes were prepared and HMGR enzyme was solubilized from the microsomes by freeze-thaw manipulation in high ionic strength buffer. The enzyme preparation was stored at $-80°$ C. in 300 µl portion samples. Prior to use, the enzyme was activated at 37° C. for 30 minutes in a reaction mixture. The reaction mixture contained in a volume of 240 µl: 0.14M potassium phosphate buffer (pH 7.0); 0.18M KCl; 3.5 mM EDTA; 10 mM dithiothreitol; 0.1 mg/ml BSA; 30,000 cpm of [$^{14}$C] HMG-CoA; 50 µM HMG-CoA, and 200 µg of solubilized enzyme with and without inhibitors (in 10 µl DMSO). After 5 minutes incubation at 37° C. the reaction was initiated with 0.2 mM NADPH. The final assay volume was 300 µl. The reaction then was terminated with 100 µl of 1N HCl. After an additional incubation for 15 minutes at 37° C. to allow for complete lactonization of the product, mevalonate, the mixture was diluted with 3 ml GDW. The diluted mixture was then poured over a 0.7×1.4 cm column containing 100–200 mesh Bio-Rex ion-exchange resin (cloride form of Bio-Rad) which was equilibrated with distilled water. With this resin the unreacted [$^{14}$C] HMG-CoA was adsorbed and the product [$^{14}$C] mevalonolactone was eluted (80% recovery) directly into scintillation vials. After the addition of 10 ml of Aquasol®, radioactivities of the samples were measured in a scintillation counter. Mevinolin (a lactone form) was then converted to its sodium salt, mevinolinic acid, by saponification in 0.1N NaOH for 60–120 minutes. Result on compound obtained in Example 1, Step 11 and compound obtained in Example 1, Step 12 is shown in Table I.

The second method (designated Ex-Vivo Non-Fasted and Ex-Vivo Fasted) used was as follows. Rats of 170–210 g were maintained on a low cholesterol diet for one week prior to use. Drugs (identified in Table I) were given orally in 0.5% methocel to both fed and fasted (fasted for 16 hours) rats. After one hour (fasted rats) and two hours (fed rats) the rats were decapitated and their livers removed and transferred to chilled oxygenated Kreb's-Ringer-bicarbonate buffer (pH 7.4). The livers were then chopped into 0.5 mm slices using a McIlwain tissue chopper, and were suspended in the same buffer. Aliquots of the suspension containing 100 mg tissue were pipetted to culture tubes which contained [$^{14}$C] sodium acetate (2 µCi, 1 mM). The tubes were gassed with 95% $O_2$/5% $CO_2$, capped and incubated at 37° C. in a shaking water bath at 150 oscillation/min. for two hours. The final assay volume was 1.0 ml. After incubation the reaction was stopped by the addition of 1.0 ml of 15% KOH in ethanol, and the internal standard 3H-cholesterol was added. The tubes were recapped and the samples were saponified at 75° C. for two hours with periodic mixing. Subsequently an aliquot was removed for protein analysis using Bie-Rads standard kit, and the remainder of the saponified samples was extracted with 10 ml of petroleum ether for 30 minutes. The lower aqueous phase was frozen in a dry ice/alcohol mixture and the ether layer was poured into labelled tubes. The ether was then evaporated to dryness and the cholesterol was separated by thin layer chromatography on plastic silica gel plates. After visualization with iodine the cholesterol spots were cut and counted with liquid scintillation fluid. Result on compound of Example 1, Step 11 is shown in Table I.

TABLE I

| | *IC$_{50}$ (Micromoles per liter) or **ED$_{50}$ (mg/kg) | | | | |
|---|---|---|---|---|---|
| Assay | Compound of Example 1 Step 11 | Compound of Example 6 Step 6 | Compound of Example 1 Step 12 | Compound of Example 5 Step 9 | Compound of Example 5 Step 8 |
| HMGR Screen | 0.15 µM | 2.0 µM | 0.0034 µM | 2.6 µM | .05 µM |
| Ex Vivo Non-Fast | 11 mg/kg | | | | |
| Ex vivo Fasted | 1.2 mg/kg | | | | |

*The micromolar concentration of compound required for 50% inhibition of cholesterol synthesis = IC$_{50}$
**The mg of drug per kg of body weight required for 50% inhibition of cholesterol synthesis = ED$_{50}$

What is claimed is:

1. Hydroxy acids and pharmaceutically acceptable salts thereof of a compound of the formula

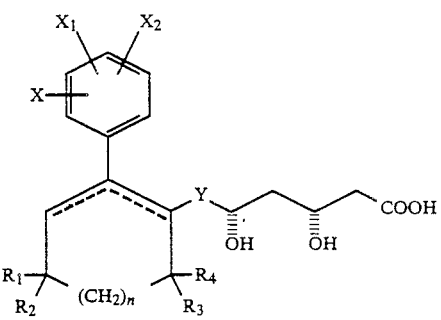

wherein

Y is
  —CHR—,
  —CHRCHR—,
  —CHRCHRCHR—, or
  —RC=CR—;
X, $X_1$ and $X_2$ are independently:
  R,
  $NO_2$,
  NH(CO)R,
  $N(R)_2$,
  $S(O)_m R$,
  F,
  Cl or
  Br;
$R_1$ is OR;
$R_2$ is R;
$R_3$ and $R_4$ are independently:
  H or
  lower alkyl;
R is
  H or
  lower alkyl;
n is 0–2; and
m is 0–2.

2. (E)-7-[2-(4-fluoro-3,5-dimethylphenyl)-4-methoxy-4-methyl-6,6-diethylcyclohex-1-en-1-yl]-3,5-dihydroxyhept-6-enoic acid sodium salt.

3. (E)-7-[2-(4-methylthio-3-methylphenyl)-4-methoxy-6,6-dimethylcyclohex-1-en-1-yl]-3,5-dihydroxyhept-6-enoic acid sodium salt.

4. (E)-7-[2-(4-acetamido-3-ethylsulfonylphenyl)-4-hydroxy-6,6-diethylcyclohex-1-en-1-yl]-3,5-dihydroxyhept-6-enoic acid.

5. A hypochloesterolemic, hypolipidemic pharmaceutical composition comprising a therapeutically effective amount of a compound of claim 1 and a pharmaceutically acceptable carrier.

6. The hypocholesterolemic, hypolipidemic pharmaceutical composition of claim 5 wherein said compound is:
(E)-7-[2-(4-fluoro-3,5-dimethylphenyl)-4-methoxy-4-methyl-6,6-diethylcyclohex-1-en-1-yl]-3,5-dihydroxyhept-6-enoic acid sodium salt.

7. The hypocholesterolemic, hypolipidemic pharmaceutical composition of claim 5 wherein said compound is selected from the group consisting of:
(E)-7-[2-(4-methylthio-3-methylphenyl)-4-methoxy-6,6-dimethylcyclohex-1-en-1-yl]-3,5-dihydroxyhept-6-enoic acid sodium salt; and
(E)-7-[2-(4-acetamido-3-ethylsulfonylphenyl)-4-hydroxy-6,6-diethylcyclohex-1-en-1-yl]-3,5-dihydroxyhept-6-enoic acid.

8. A method of inhibiting cholesterol biosynthesis in a patient in need of such treatment comprising administering a pharmaceutical composition defined in claim 5.

* * * * *